(12) United States Patent
Miller et al.

(10) Patent No.: US 9,877,986 B2
(45) Date of Patent: *Jan. 30, 2018

(54) PORTABLE, NITRIC OXIDE GENERATOR

(71) Applicant: SYK TECHNOLOGIES, LLC, Newport Beach, CA (US)

(72) Inventors: J. W. Randolph Miller, Orem, UT (US); William Moon, Provo, UT (US); Keith L. Merrell, Bountiful, UT (US)

(73) Assignee: SYK TECHNOLOGIES, LLC, Newport Beach, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/460,096

(22) Filed: Mar. 15, 2017

(65) Prior Publication Data

US 2017/0246203 A1   Aug. 31, 2017

Related U.S. Application Data

(60) Division of application No. 14/847,183, filed on Sep. 8, 2015, now Pat. No. 9,629,871, which is a division
(Continued)

(30) Foreign Application Priority Data

Dec. 10, 2002 (CA) ..................... 2413834

(51) Int. Cl.
*A61K 33/00* (2006.01)
*B01J 7/00* (2006.01)
*C01B 21/24* (2006.01)

(52) U.S. Cl.
CPC ............... *A61K 33/00* (2013.01); *B01J 7/00* (2013.01); *C01B 21/24* (2013.01); *B01J 2219/00135* (2013.01)

(58) Field of Classification Search
CPC ....................................... A61K 33/00
See application file for complete search history.

(56) References Cited

U.S. PATENT DOCUMENTS 2,310,907 A   2/1943   Mcmillian
4,142,508 A   3/1979   Watson
(Continued)

FOREIGN PATENT DOCUMENTS

JP   61171998   2/1986
JP   63187196   8/1988
(Continued)

OTHER PUBLICATIONS

Ray et al, a new method of preparing nitric oxide, 1956, p. 5993.*
(Continued)

*Primary Examiner* — Melvin C Mayes
*Assistant Examiner* — Stefanie Cohen
(74) *Attorney, Agent, or Firm* — Pate Baird, PLLC

(57) ABSTRACT

An apparatus for portable delivery of nitric oxide without the need for pressurized tanks, power supplies, or other devices provides a single therapy session by triggering a heater to heat a reaction chamber. A piercing assembly may trigger to open sealed containers, such as bags, of liquid water or salt water in order to activate the heaters. Upon addition of liquid such as water or salt water to a chemically reactive heating element, heat is generated to activate the chemicals generating nitric oxide within a sealed reactor. Upon triggering, liquid containers are unsealed, the liquid drains down to initiate reaction of the heating chemicals, and the heat begins to penetrate the reactor. The reactor, in turn, heats its contents, which react to form nitric oxide expelled by the reactor to a line feeding a cannula for therapy.

16 Claims, 21 Drawing Sheets

Related U.S. Application Data of application No. 12/419,123, filed on Apr. 6, 2009, now Pat. No. 9,138,707, which is a continuation-in-part of application No. 11/751,523, filed on May 21, 2007, now Pat. No. 7,939,045, which is a continuation-in-part of application No. 10/733,805, filed on Dec. 10, 2003, now Pat. No. 7,220,393.

(60) Provisional application No. 61/043,064, filed on Apr. 7, 2008.

(56) References Cited

U.S. PATENT DOCUMENTS

| | | | |
|---|---|---|---|
| 4,943,066 A | 7/1990 | Lathim et al. | |
| 5,063,050 A | 11/1991 | Verdon et al. | |
| 5,427,797 A | 6/1995 | Frostell et al. | |
| 5,485,827 A | 1/1996 | Zapol et al. | |
| 5,560,919 A | 10/1996 | Morikawa et al. | |
| 5,648,101 A | 7/1997 | Tawashi | |
| 5,713,349 A | 2/1998 | Keaney | |
| 5,813,932 A | 9/1998 | Grafton | |
| 5,823,180 A | 10/1998 | Zapol | |
| 5,839,433 A | 11/1998 | Higgenbottam | |
| 5,873,359 A | 2/1999 | Zapol | |
| 5,900,433 A | 5/1999 | Igo et al. | |
| 6,000,403 A | 12/1999 | Cantwell | |
| 6,001,279 A | 12/1999 | Payzant et al. | |
| 6,019,100 A | 2/2000 | Alving et al. | |
| 6,063,407 A | 5/2000 | Zapol et al. | |
| 6,103,275 A | 8/2000 | Seitz et al. | |
| 6,131,572 A | 10/2000 | Heinonen | |
| 6,142,147 A | 11/2000 | Head et al. | |
| 6,149,606 A | 11/2000 | Alving et al. | |
| 6,432,077 B1 | 8/2002 | Stenzler | |
| 6,458,109 B1 | 10/2002 | Henley et al. | |
| 6,572,594 B2 | 6/2003 | Satterfield et al. | |
| 6,581,599 B1 | 6/2003 | Stenzler | |
| 6,601,580 B1 | 8/2003 | Bloch et al. | |
| 6,612,306 B1 | 9/2003 | Mault | |
| 6,670,323 B1 | 12/2003 | Looker et al. | |
| 6,689,810 B2 | 2/2004 | Martin | |
| 6,786,217 B2 | 9/2004 | Stenzler | |
| 6,793,644 B2 | 9/2004 | Stenzler | |
| 7,017,573 B1 | 3/2006 | Rasor et al. | |
| 7,045,152 B2 | 5/2006 | Stamler | |
| 7,048,951 B1 | 5/2006 | Seitz et al. | |
| 7,122,018 B2 | 10/2006 | Stenzler et al. | |
| 7,220,393 B2 | 5/2007 | Miller et al. | |
| 9,138,707 B2 * | 9/2015 | Miller | B01J 7/00 |
| 9,629,871 B2 * | 4/2017 | Miller | B01J 7/00 |
| 2001/0037810 A1 | 11/2001 | Fine et al. | |
| 2002/0110590 A1 | 8/2002 | Shaked et al. | |
| 2003/0062043 A1 | 4/2003 | Fine et al. | |
| 2003/0064115 A1 | 4/2003 | Fine et al. | |

FOREIGN PATENT DOCUMENTS

| | | |
|---|---|---|
| WO | 2006/110923 | 10/2006 |
| WO | 2007/057763 | 5/2007 |

OTHER PUBLICATIONS

Ray, James D., Ogg Jr., Richard A. "A New Method of Preparing Nitric Oxide" Department of Chemistry, Stanford University, as early as Jul. 25, 1956.

"VIASYS Healthcare Inc. and INO Therapeutics, LLC Reach Settlement" Business Wire, May 14, 2004, pp. 1-2, Conshohocken, PA and Clinton, N.J., http://findarticles.com/p/articlesmi_m0EIN/is_2004_May_14/ai_n6028801.

"Guidance for Industry and for FDA Reviews—Guidance Document for Premarket Notification Submissions for Nitric Oxide Delivery Apparatus, Nitric Oxide Analyzer and Nitrogen Dixoide Analyzer", U.S. Food and Drug Administration Center for Devices and Radiological Health, Jan. 24, 2000, Updated Mar. 29, 2007, pp. 1-34, http://www.fda.gov/cdrh/ode/1157.html.

* cited by examiner

Section A-A

PORTABLE, NITRIC OXIDE GENERATOR

RELATED APPLICATIONS

This patent application is a divisional of U.S. patent application Ser. No. 14/847,183, filed Sep. 8, 2015, issued as U.S. Pat. No. 9,629,871, which is a divisional of U.S. patent application Ser. No. 12/419,123, filed Apr. 6, 2009, issued as U.S. Pat. No. 9,138,707, which claims the benefit of U.S. Provisional Patent Application Ser. No. 61/043,064, filed Apr. 7, 2008, and is a continuation in part of U.S. patent application Ser. No. 11/751,523, filed May 21, 2007, issued as U.S. Pat. No. 7,939,045, on May 10, 2011, which is a continuation-in-part of U.S. patent application Ser. No. 10/733,805, filed Dec. 10, 2003, issued as U.S. Pat. No. 7,220,393, on May 22, 2007, which claims the benefit of Canadian Patent Application Serial No. 2,413,834, filed Dec. 10, 2002. All of the foregoing applications and patents are hereby incorporated by reference in their entirety.

BACKGROUND

1. The Field of the Invention

This invention relates generally to chemical reactors, and more specifically to apparatus and methods for generating nitric oxide.

2. Background

The discovery of certain nitric oxide effects in live tissue garnered a Nobel prize. Much of the work in determining the mechanisms for implementing and the effects of nitric oxide administration are reported in literature. In its application however, introduction of bottled nitric oxide to the human body has traditionally been extremely expensive. The therapies, compositions, and preparations are sufficiently expensive to inhibit more widespread use of such therapies. What is needed is a comparatively inexpensive mechanism for introducing nitric oxide in a single dosage over a predetermined period of time. Also, what is needed is a simple introduction method for providing nitric oxide suitable for inhaling.

It would be an advance in the art to provide a single dose generator suitable for administration of nitric oxide gas. It would be an advance in the art to provide not only an independence from bottled gas, but from the need for a source of power for heat, or the like. It would be a further advance in the art to provide a disposable generator to be initiated by a trigger mechanism and operate without further supervision, adjustment, management, or the like. Likewise, it would be a substantial benefit to provide a system that requires a minimum of knowledge or understanding of the system, which might still be safe for an individual user to administer with or without professional supervision.

BRIEF SUMMARY OF THE INVENTION

In accordance with the foregoing, certain embodiments of an apparatus and method in accordance with the invention provide a self-contained reactor system. Nitric oxide may thus be introduced into the breathing air of a subject. Nitric oxide amounts may be engineered to deliver a therapeutically effective amount on the order of a comparatively low hundreds of parts per million, or in thousands of parts per million. For example, sufficient nitric oxide may be presented through nasal inhalation to provide approximately five thousand parts per million in breathing air. This may be diluted due to additional bypass breathing through nasal inhalation or through oral inhalation.

One embodiment of an apparatus and method in accordance with the present invention may rely on a small reactor. Reactive solids may be appropriately combined dry. Reactants may include compounds, such as potassium nitrite, sodium nitrite, or the like, nitrate compounds, such as potassium nitrate, sodium nitrate, or the like. The reaction may begin upon introduction of a heat. Heat may be initiated by liquid transport material to support ionic or other chemical reaction in a heat device.

An apparatus and method in accordance with the invention may include an insulating structure, shaped in a convenient configuration such as a rectangular box, a cylindrical container, or the like. The insulating container may be sealed either inside or out with a containment vessel to prevent leakage of liquids therefrom. Such a system need not be constructed to sustain nor contain pressure. Inside the containment vessel may be positioned heating elements such as those commercially available as chemical heaters.

In certain embodiments, chemical heaters may include metals finely divided to readily react with oxygen or solid oxidizers. Various other chemical compositions of modest reactivity may be used to generate heat readily without the need for a flame, electrical power, or the like.

Above the heating element or heater within the containment vessel may be located a reactor. The reactor may preferably contain a chemically stable composition for generating nitric oxide. Such compositions, along with their formulation techniques, shapes, processes, and the like are disclosed in U.S. patent application Ser. No. 11/751,523 and U.S. Pat. No. 7,220,393, both incorporated herein by reference in their entireties as to all that they teach.

The reactor may include any composition suitable for generating nitric oxide by the activation available from heat. The reactor may be substantially sealed except for an outlet, such as a tubular member secured thereto to seal a path for exit of nitric oxide from the reactor.

In certain embodiments, a system of water or salt water may be available in the container. In one embodiment, the water containers may be as simple as presealed bags, such as polyethylene bags that can be opened, cut, torn, or otherwise pierced in order to release water therefrom. Accordingly, a system may include a heating element or the reactor, such a water source to provide a chemical transport fluid, a piercing assembly for the water containers, a trigger for activating the piercing assembly, and blades, hooks, cutters, punches, or the like structured to open the bags containing water.

Upon triggering of the piercing assembly, the water is released from the water containers, vessels, bags, or the like, to be poured down through the assembly onto the heating elements where heaters are activated by the presence of a liquid. It has been found through experiments that adding the additional ionic content of salt improves the reaction rate of chemical heating systems.

Ultimately, an apparatus in accordance with the invention may include a cover through which an outlet penetrates from the reactor in order to connect to a cannula. This has been done effectively. It will also support a vent for steam generated by the heaters in the presence of the water used to activate the heaters. The system may be completely wrapped in a pre-packaged assembly. In one embodiment, a heat-shrinkable wrapping material may be used to seal the outer container of an apparatus in accordance with the invention. Thus, this system may be rendered tamper proof, while also being maintained in integral condition throughout its distribution, storage, and use.

BRIEF DESCRIPTION OF THE DRAWINGS

The foregoing features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

DETAILED DESCRIPTION OF THE PREFERRED EMBODIMENTS

Figure 1:
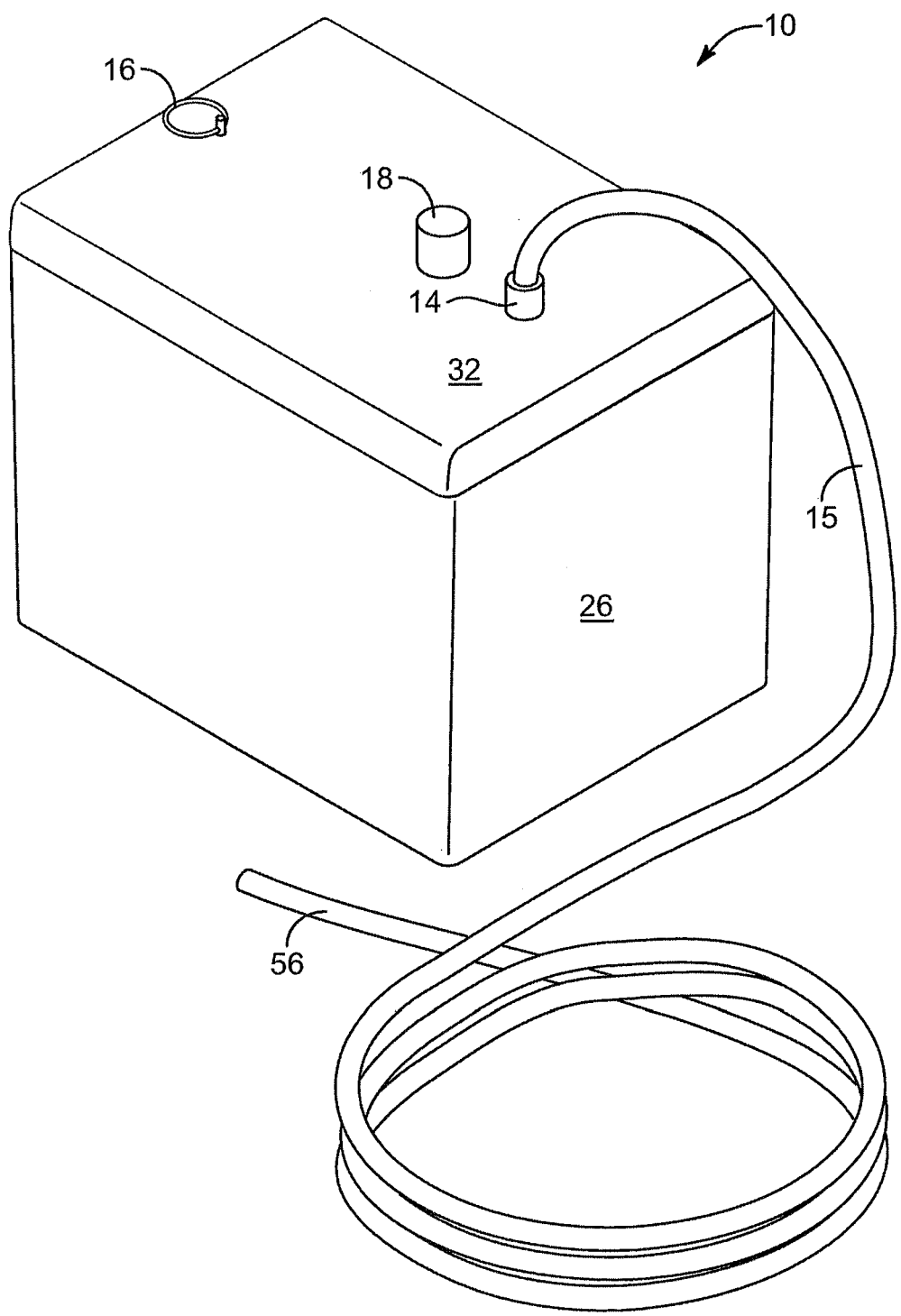
FIG. 1 is a perspective view of one embodiment of an apparatus in accordance with the invention to generate nitric oxide from a chemically active source of nitric oxide, as a result of exposure to heat.

It will be readily understood that the components of the present invention, as generally described and illustrated in the drawings herein, could be arranged and designed in a wide variety of different configurations. Thus, the following more detailed description of the embodiments of the system and method of the present invention, as represented in the drawings, is not intended to limit the scope of the invention, as claimed, but is merely representative of various embodiments of the invention. The illustrated embodiments of the invention will be best understood by reference to the drawings, wherein like parts are designated by like numerals throughout.

Referring to FIG. 1, an apparatus 10 may be configured as a portable nitric oxide device. In the illustrated embodiment, a container 12 or vessel 12 may provide insulation, liquid sealing, or both. Meanwhile, a fitting 14 or outlet 14 may be connected to feed nitric oxide to a line 15 proceeding toward a user, for distribution by a cannula, mask, tent, or the like.

In the illustrated embodiment, a trigger 16 or actuator 16 may be withdrawn from the apparatus 10 in order to trigger the initiation of a reaction generating nitric oxide. In certain embodiments, generation of nitric oxide may depend on temperature of reactants. The generation of heat (e.g., temperature) may rely on a reaction requiring moisture, which moisture may eventually be partially converted to steam needing to be vented. Accordingly, a vent 18 may vent the interior of the container 12 in order to avoid any buildup of pressure; in one embodiment, the entire container 12 may be sealed in a heat-shrinkable sleeve that maintains the integrity of the apparatus 10 during distribution, storage, and use.

Figure 2:
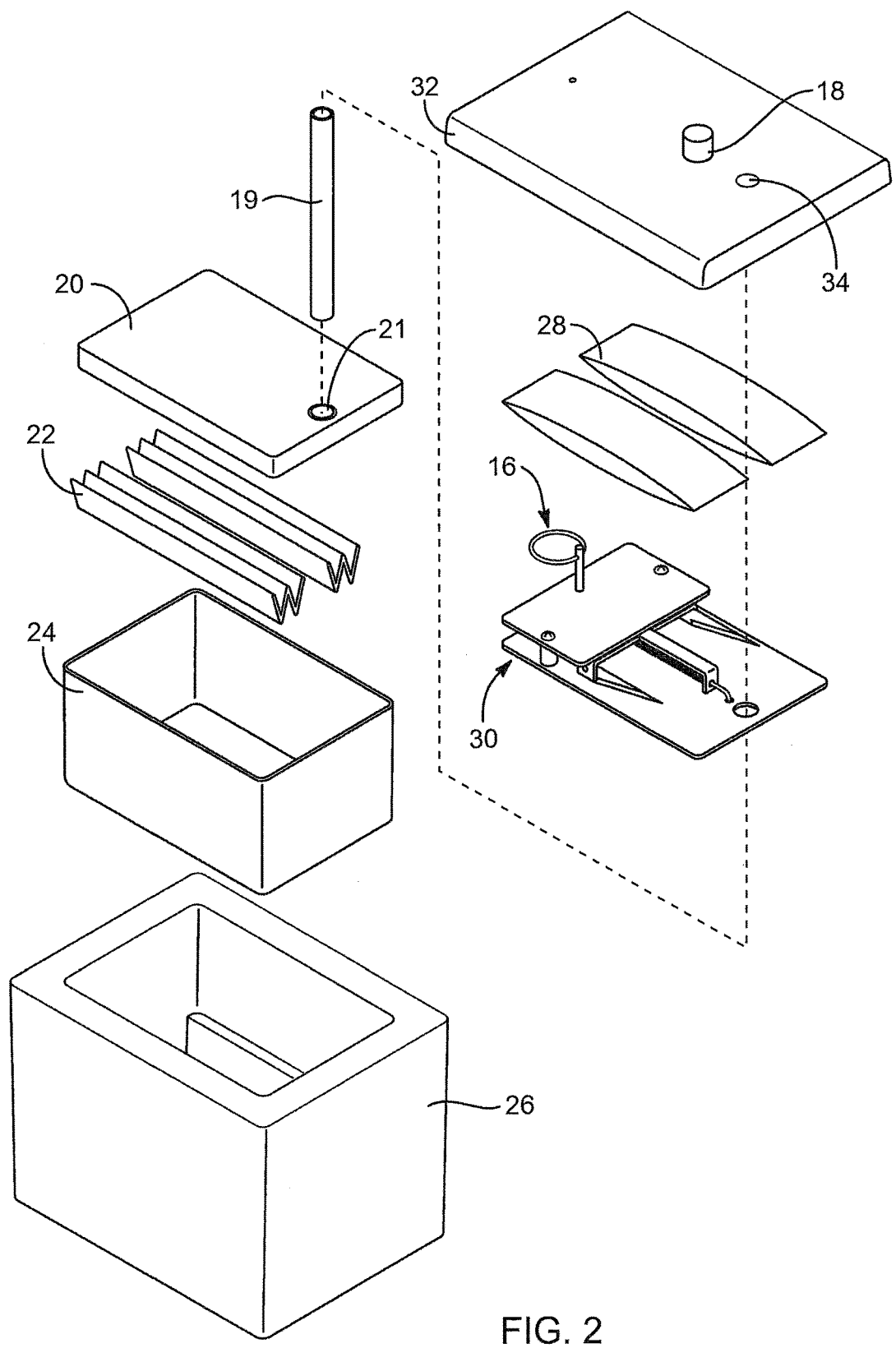
FIG. 2 is an exploded view of the apparatus of FIG. 1 for generating nitric oxide.
Figure 3:
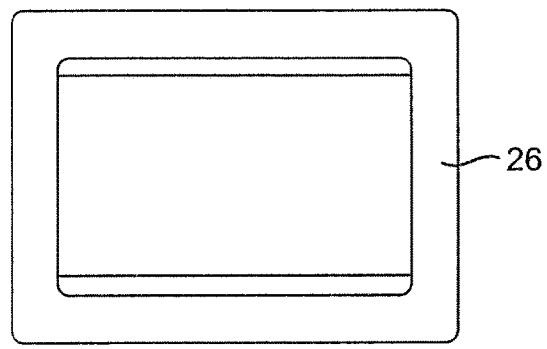
FIG. 3 is a top plan view of an insulating container for the apparatus of FIG. 1.
Figure 5:
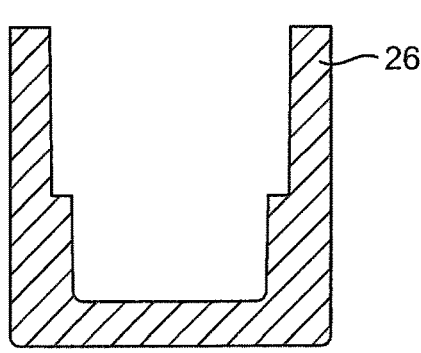
FIG. 5 is an end, elevation, cross-sectional view of the container (box) of FIGS. 3-4.
Figure 4:
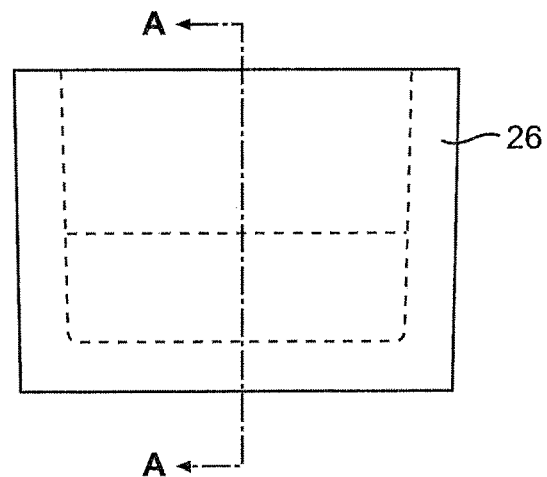
FIG. 4 is a side elevation view of the box-like container of FIG. 3.
Figure 7:
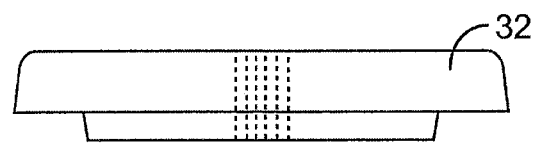
FIG. 7 is an end elevation view of the cover of FIG. 6.
Figure 8:
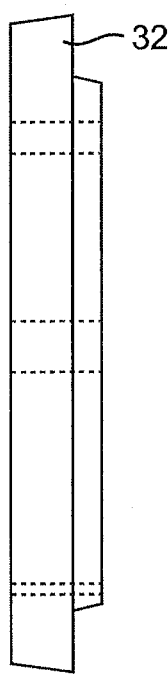
FIG. 8 is a side elevation view of the cover of FIG. 6.
Figure 6:
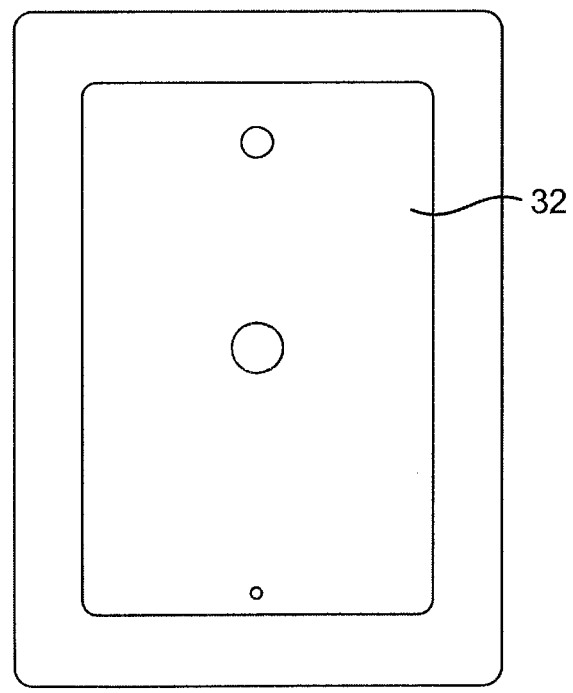
FIG. 6 is a top plan view of a cover for the container of FIGS. 3-5.
Figure 9:
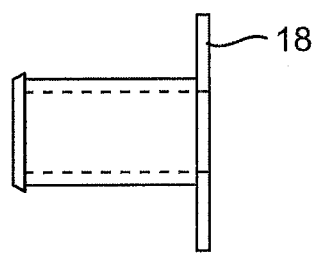
FIG. 9 is a side elevation view of a vent for the portable nitric oxide device of FIG. 1.
Figure 10:
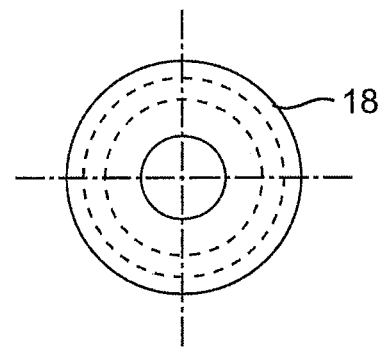
FIG. 10 is a top plan view of the vent illustrated in FIG. 9.
Figure 12A:
FIG. 12a is an end view of the pin of FIG. 11.
Figure 11:
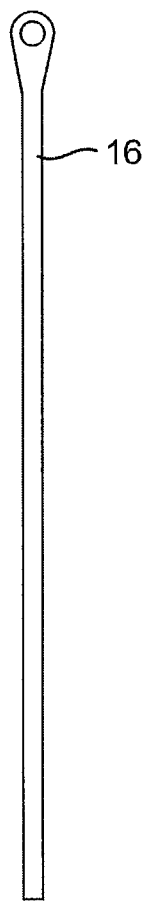
FIG. 11 is a front elevation view of a triggering pin for the apparatus of FIG. 1.
Figure 12B:
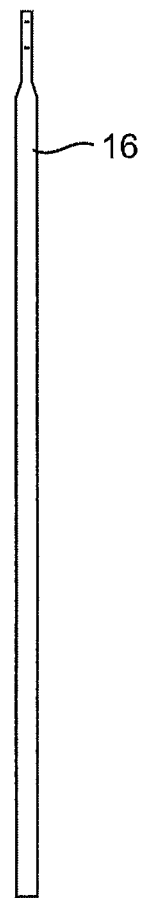
FIG. 12b is a side elevation view of the pin of FIG. 11.
Figure 13:
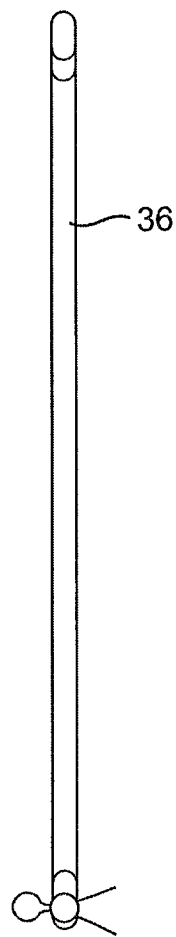
FIG. 13 is a bottom plan view of a guiding rod for holding a compression spring used in the trigger device of the apparatus of FIG. 2.
Figure 14:
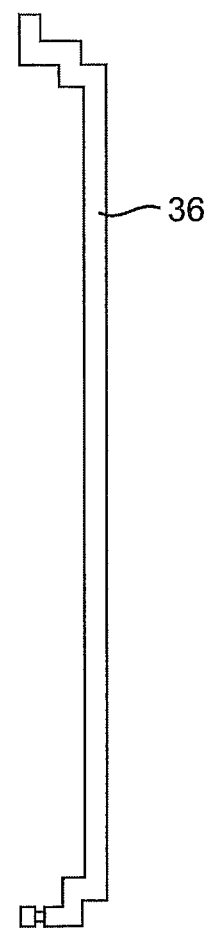
FIG. 14 is a side elevation view of the guide rod of FIG. 13.
Figure 15:
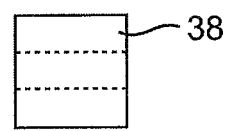
FIG. 15 is a front elevation view of a spacer used in the piercing assembly of FIG. 2.
Figure 16:
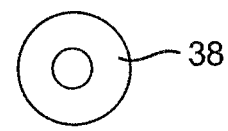
FIG. 16 is a top plan view of the spacer of FIG. 15.
Figure 17:
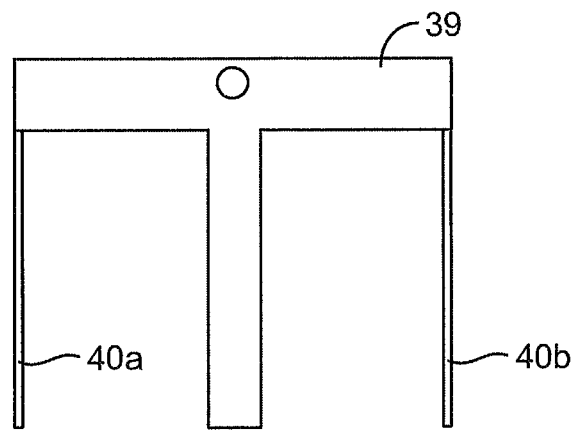
FIG. 17 is a top plan view of the mounting assembly for a blade of the piercing assembly of the apparatus of FIG. 2.
Figure 19:
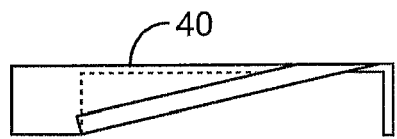
FIG. 19 is a side elevation view of the mounting assembly with blades in place, and corresponds to the apparatus illustrated in FIGS. 17-18.
Figure 18:
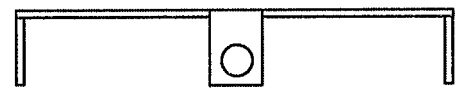
FIG. 18 is an end elevation view of the mounting assembly or carrier for blades in the piercing assembly of FIG. 2, and corresponds to the apparatus of FIG. 17.
Figure 20:
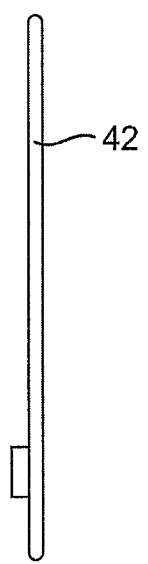
FIG. 20 is a side elevation view of a base or base plate for supporting the blades in the piercing assembly of the apparatus of FIG. 2.
Figure 21:
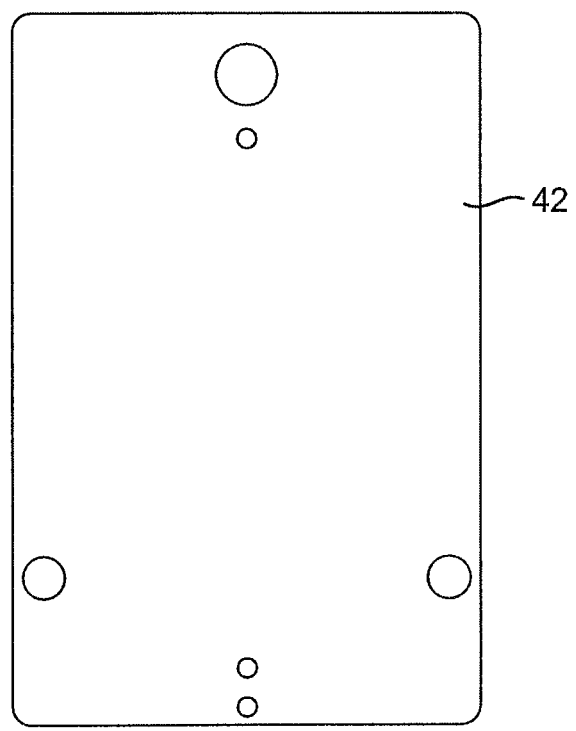
FIG. 21 is a top plan view of the base or base plate of the apparatus of FIG. 20.
Figure 22:
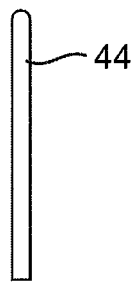
FIG. 22 is a side elevation view of a cover plate for the blades in the piercing assembly of the apparatus of FIG. 2.
Figure 23:
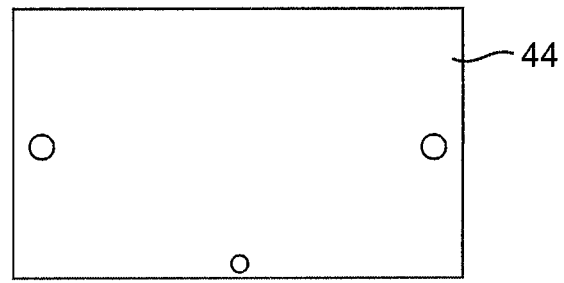
FIG. 23 is a top plan view of the cover plate of FIG. 22.
Figure 24:
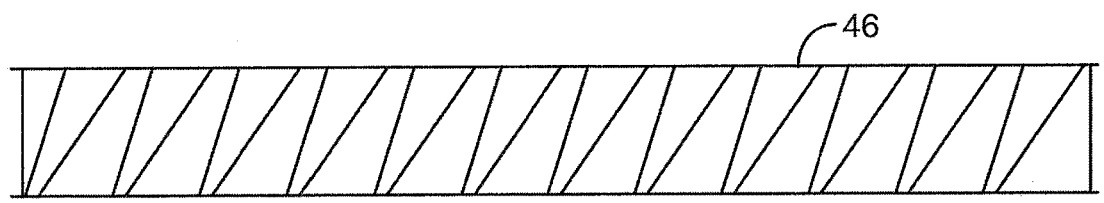
FIG. 24 is a side elevation view of a spring, used as a compression spring to drive the mounting assembly of FIG. 17, with the blades installed to operate the piercing assembly of FIG. 2.
Figure 26:
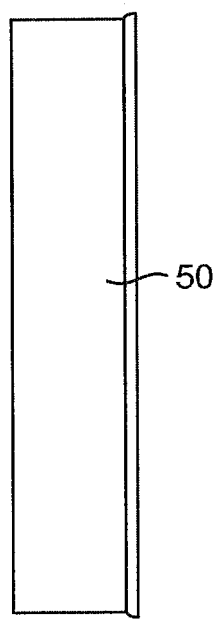
FIG. 26 is a side elevation view of the reactor's containment vessel of FIG. 25.
Figure 25:
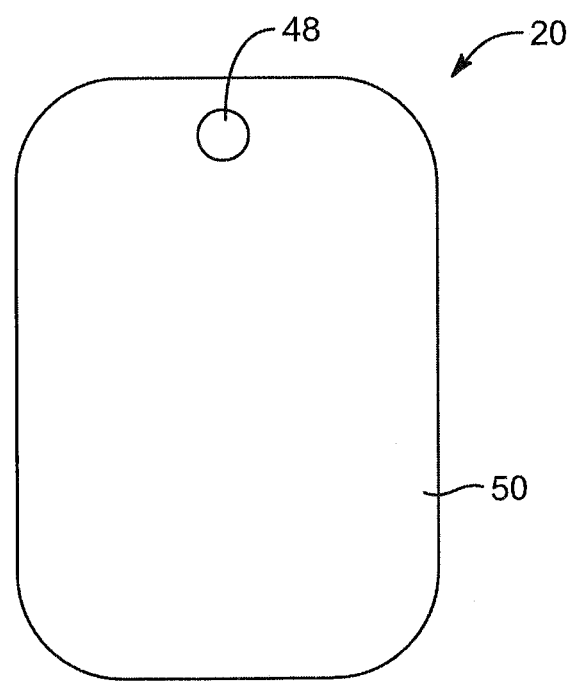
FIG. 25 is a top plan view of one embodiment of a containment vessel operating as a reactor for the nitric oxide generation from the chemical species contained therein.
Figure 27:
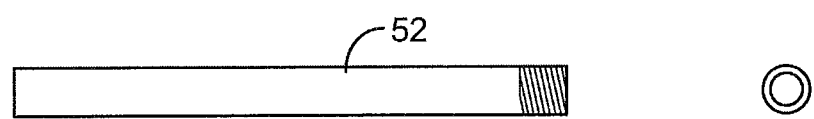
FIG. 27 is a side elevation view of one embodiment of a tube configured to operate as an outlet for the reactor vessel of FIG. 25.
Figure 28:
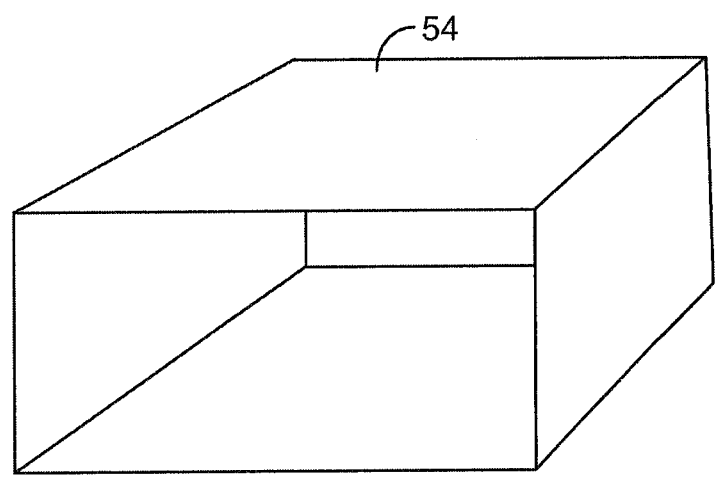
FIG. 28 is a perspective view of one embodiment of a shrink-wrap sleeve that is applied to contain the overall enclosure of the apparatus of FIGS. 1-2.
Figure 29:
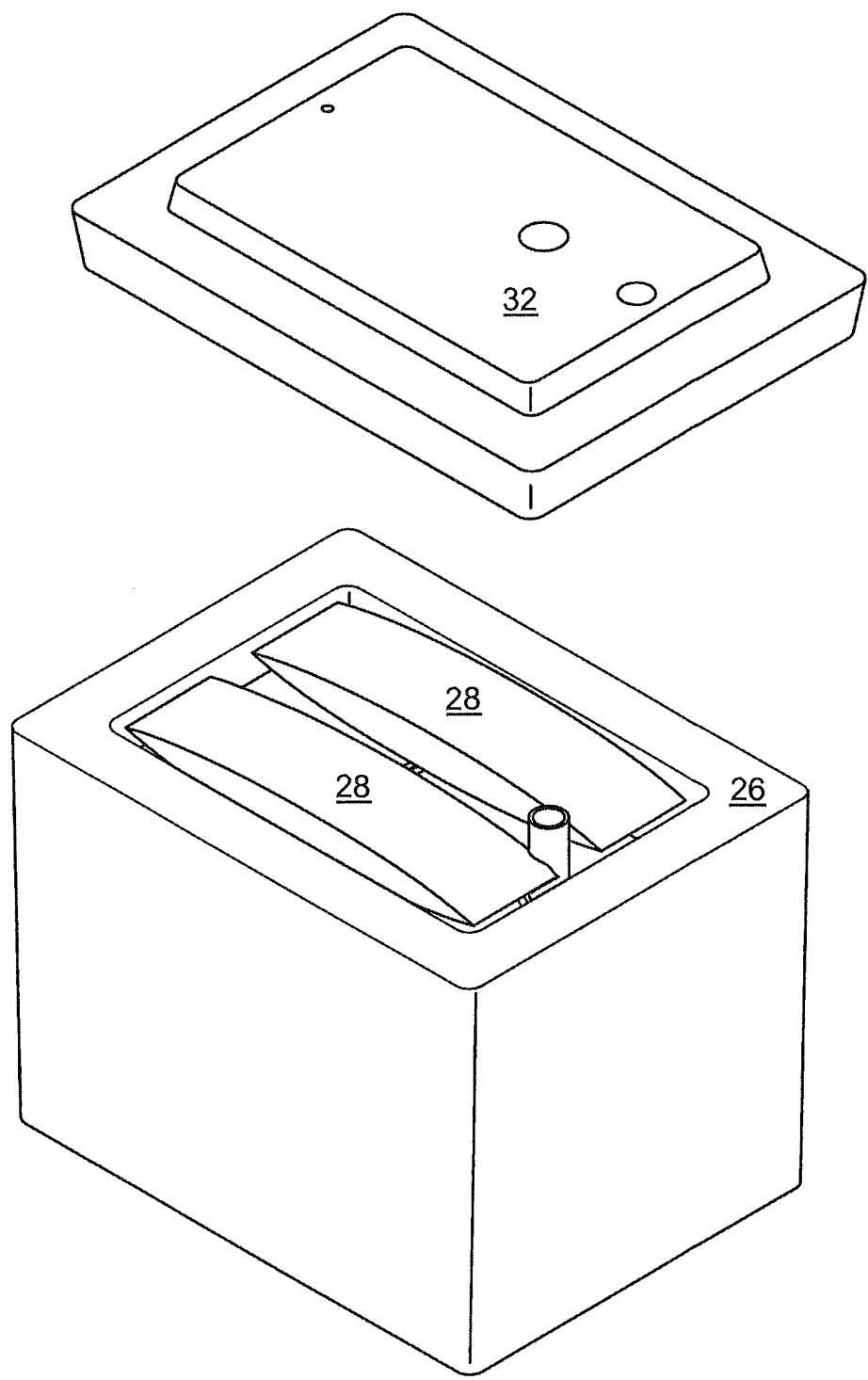
FIG. 29 is a perspective view of the apparatus of FIGS. 1-2.
Figure 30:
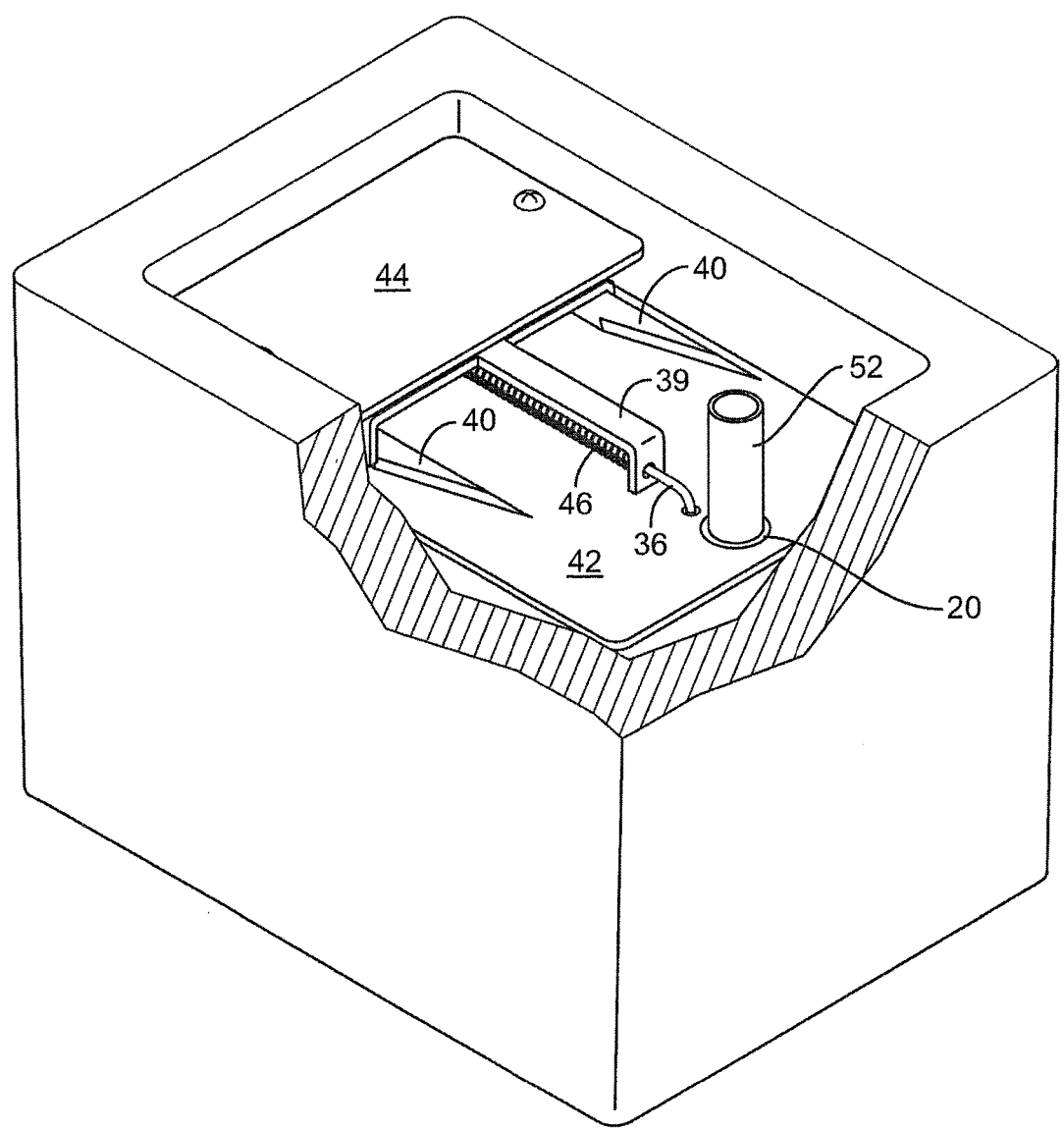
FIG. 30 is a top view of the apparatus of FIG. 29 open for viewing of the internal apparatus.

Referring to FIG. 2, an exploded view of the apparatus of FIG. 1 illustrates one embodiment of the apparatus 10 in accordance with the invention. In the illustrated embodiment, the outlet 19, connected to feed through the fitting 14 and thus feed nitric oxide through the line 15 may be securely sealed to a reactor 20. The reactor 20 may be formed by any of several suitable methods to contain the chemical constituents required to generate nitric oxide. A port 21 or aperture 21 may be formed to seal against the outlet 19 in order to discharge all of the generated nitric oxide to a location outside the apparatus 10.

Below or around the reactor 20 may be located one or more heaters 22 or heating elements 22. In the illustrated embodiment, the heaters 22 are formed to contain solid reactants in a non-woven fabric container. The reactants are stabilized by being completely dry. In the presence of liquid, ionic exchange promotes the reaction of the contained chemicals within the heaters 22.

In order to contain any liquid to activate the heaters 22, a containment vessel 24 may surround the heaters 22, within the insulation container 26 or box 26. In certain embodiments, the functionality of the containment vessel 24 and the insulated container 26 may be consolidated into a single structure. Likewise, in certain embodiments, the containment vessel 24 may actually be located external to the insulated container 26.

In general, a liquid, and particularly a hydrating liquid such as water, salt water, or the like, may serve as an activation material. In the illustrated embodiment, the bags 28 containing salt water, water, or the like may be sealed for storage. In certain embodiments, the containers 28 may be capped, vented, or otherwise made resealable. However, in other embodiments, a fully disposable apparatus 10 may rely on inexpensive materials such as polyethylene film to form the containers 28.

By any means, an opening assembly 30 (in the illustrated embodiment, a piercing assembly 30) may be actuated to open, pierce, or otherwise breach the sealing of the containers 28 of liquid. Upon piercing or otherwise breaching of the integrity of the containers 28, the contained liquid then flows downward to be absorbed within the covering material of the heaters 22. The presence of the liquid activates the chemical reactions within the heaters 22, generating heat to initiate reaction of the chemical constituents contained within the reactor 20.

A cover 32 may enclose the insulated container 26, and may typically be formed of the same material. A vent 30 may vent steam from within the containment vessel 24 and the insulated container 26 in order to alleviate any pressure build up. Likewise, in order to direct the residual steam in a specific direction other than permitting it to escape about the interface between the cover 32 and the container 26, a vent 18 may be advisable, required, or otherwise useful.

The outlet 19 for nitric oxide may penetrate through the cover 32 by means of an aperture 34. The aperture 34 may be sealed against the outlet 19 in order that the steam generated from the heaters 22 escape substantially exclusively through the vent 18, rather than near the fitting 14 and line 15 that may be subject to manipulation by the user.

Referring to FIGS. 3-8 and 29, but referring generally to FIGS. 3 through 24, the insulated container 26 may be formed in any suitable shape to contain all of the elements required for a single dosing of nitric oxide. Accordingly, the constituent structures of FIG. 2 may fit within the interior of the container 26. Meanwhile, the cover 32 may be fitted thereto.

The vent 18 may be formed to fit snugly through a penetration in the cover 32. A flange thereof may be labeled with colors and text appropriate to warn of the elevated temperature thereof as a safety measure.

A pin may act as a significant portion of the trigger assembly 16 or trigger 16. Upon removal of the pin, such as by a user pulling on a handle or ring secured thereto, the blades may be released to pierce the containers 28 holding the liquid required to initiate the reaction of heaters 22.

A guide 36 or guide rod 36 may direct the blades of the piercing assembly 30. A compression spring wrapped around the guide 36 or rod 36 may push the blades forward. Referring to FIGS. 13-23, generally, while specifically referring to FIGS. 15-16, the piercing assembly 30 may be configured to protect against inadvertent exposure to sharp instruments. A spacer 38 may provide room for operation of a blade assembly 39 or mount 39 holding blades 40 secured thereto.

For example, a "T"-shaped mounting assembly may secure two blades 40a, 40b that will eventually slide parallel to the base of the T, and along the same direction of the guide 35 or guide rod 36. In the illustrated embodiment, an aperture in the foot of the T-shaped mount may run along the guide rod 36, driven by the compression spring acting along the length of the rod 36.

The blade assembly or mount 39, together with its attached blades 40 may operate by sliding along an upper surface of the baseplate 42. Two apertures on opposing sides or near opposing edges of the baseplate 42 may receive fasteners to penetrate a pair of corresponding spacers 38. The spacers 38 form a clearance above the baseplate 42 for operation of the mount 39.

A cover 44 or cover plate 44 may include a pair of apertures at or near opposing edges thereof to receive the same fasteners that penetrate the baseplate 42. Accordingly, the cover plate 44, or simply cover 44, is spaced away from the baseplate 42 sufficient distance to receive the mount 39 and attached blades 40 therewithin. Thus, the blade assembly 39 or mount 39 with its attached blades 40 is effectively "garaged" between the baseplate 42, and the cover plate 44. Meanwhile, a compression spring 46 pushes against the base of the T-shaped mount 39, driving the aperture therein along the guide rod 36 captured in the aperture.

A reactor 20 may include a principal containment vessel 50. In one embodiment, a conventional "tin," or metal can, may be formed by conventional technology available for canning. In other embodiments, the reactor 20 may rely on other structures such as fiber-reinforced composites, cylinders, sealed and flexible but inextensible lattice work, fabrics, or the like, in order to contain the chemical constituents reacting to form nitric oxide.

In one embodiment, tablets, granules, or other configurations of reactants may be placed in a can, sealed to form the reactor vessel 50. An aperture 40 in the vessel 50 may receive a tube 52 acting as a reactor outlet 19. The outlet 19 may conduct nitric oxide generated within the containment vessel 50 to a location outside the insulated container 26 in order to deliver to a line 15.

Various mechanisms may be available for maintaining the integrity of the apparatus 10. In one embodiment, a heat shrinkable wrapping material may be formed in a seamless sleeve. The sleeve may be placed around the apparatus 10, and judiciously penetrated to accommodate the fitting 14, the vent 18, the trigger 16, and so forth. Thereupon, the sleeve 54 may be heated in order to shrink it snugly about the insulated container 26. Thereafter, any breach of the sleeve 54 indicates a lack of integrity of the apparatus 10.

One embodiment of an apparatus 10 in accordance with the invention was formed using expanded polystyrene for the insulated container 26. A fitting 14 to receive a line 15 delivering nitric oxide to a cannula 56 received nitric oxide from a reactor 20 within the insulated container 26. A vent 18 penetrated the cover 32 of the insulated container 26 to vent steam. A trigger mechanism 16 penetrated the cover 32 in order to reach the piercing assembly 30 described hereinabove.

Containers 28 filled with salt water were provided and placed above the piercing assembly 30 and the reactor 20 therebelow. The heaters 22 were placed entirely below the reactor 20, although they may also be wrapped therearound, or even placed on top. However, inasmuch as the heaters 22 tend to vaporize some of the liquid in the containers 28 when released, the heated steam generated below the reactor was effective to heat the reactor 20. Steam rising from heaters thereabove would not ever be in contact with the heaters 22. That is, heat rising with steam originating above the reactor 20, will not contribute as much heat to the reactor 20. The outlet 14 from the reactor was formed of a stainless steel tube 52 penetrating the reactor 20.

The blades 40 were positioned between the baseplate 42, and the cover plate 44. The guide rod 36 was secured to the baseplate 42 to maintain alignment of the mount 39 as the spring 46 drove the mount 39 forward along the guide rod 36. Upon release of a trigger 16, the mount 39 advanced out from under the cover plate 44, exposing the containers 28 to the sharp blades 40. The blades 40 compromised the containers 28 from below, thus substantially evacuating all the water therefrom. In the experiment illustrated, salt water was used as the liquid within the containers 28. In some experiments, a single container was used. In other embodiments, including experiments conducted, multiple containers 28 filled with liquid were used.

In one embodiment, a method of producing nitric oxide may comprise the following steps. A mixture of reactants may be provided consisting essentially of potassium nitrate, sodium nitrite, and chromic oxide. The chromic oxide may be calcined to remove substantially all water bonded thereto. The reactants may be placed in a vessel, or reactor, and any moisture in the vessel may be substantially evacuated. The reactants in the vessel may be heated to a temperature selected to initiate a reaction generating nitric oxide gas. The nitric oxide gas generated may be drawn from the vessel at negative gauge pressure to substantially preclude further heating and limit further reaction, or any secondary reactions, of the nitric oxide gas. The nitric oxide gas may be cooled and mixed with a diluent gas to form a mixture breathable by a subject. The breathable mixture may be regulated to substantially ambient temperature and pressure and delivered to the subject to provide a therapeutically safe and effective concentration of nitric oxide gas.

Figure 31:
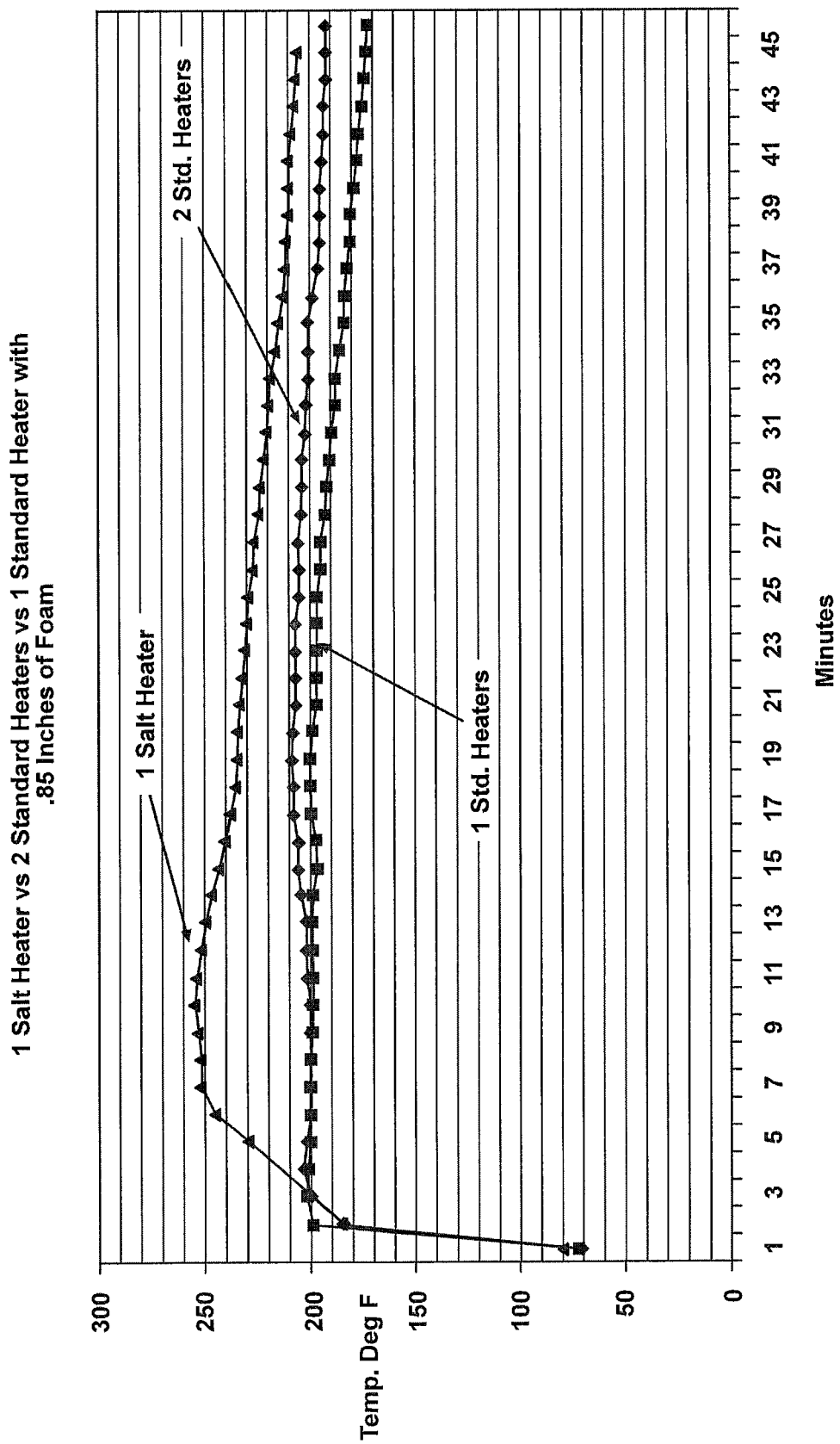
FIG. 31 is a graph showing data for the temperature rise in degrees Fahrenheit of the reactor of FIGS. 29 and 30 using a variety of heaters including a single heater relying on water as the liquid, two standard heaters relying on water, and a single heater using salt water as the activating liquid.

Referring to FIG. 31, in one set of experiments, a single standard heater was used with water, as indicated. In other experiments, multiple heaters 22 were used. In yet other experiments, a single heater was used, but the liquid used to activate the heater 22, was salt water. The chart illustrates the substantial temperature increase due to the use of the ionized salt within the salt water. Throughout the course of the experiment, the temperature was observably higher, and in some instances substantially higher, when salt water was the electrolyte initiating the reaction in the heaters 22. Moreover, a single heater provided more temperature rise in the reactor 20 than twice that amount of chemical (two standard heaters), relying only on water alone as the electrolyte.

Figure 32:
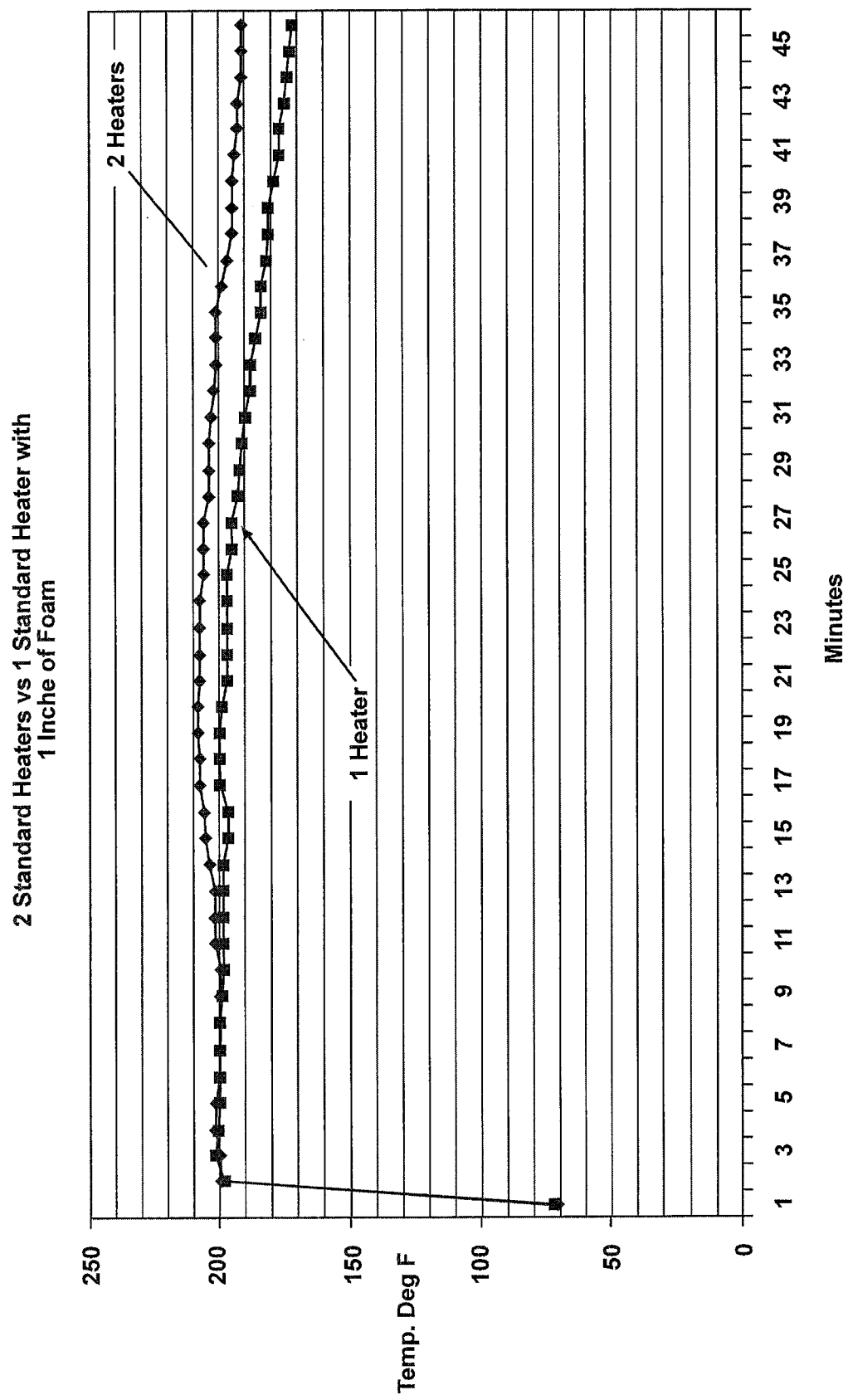
FIG. 32 is a graph depicting the temperature response of the reactor of FIGS. 1-30 over time in both a single heater and double heater configuration.

Referring to FIG. 32, one may see that the insulation value of the insulated container 26 has some effect. Nevertheless, in general, a more pronounced effect over the latter part of the subject time results from the addition of a second heater 22.

Figure 33:
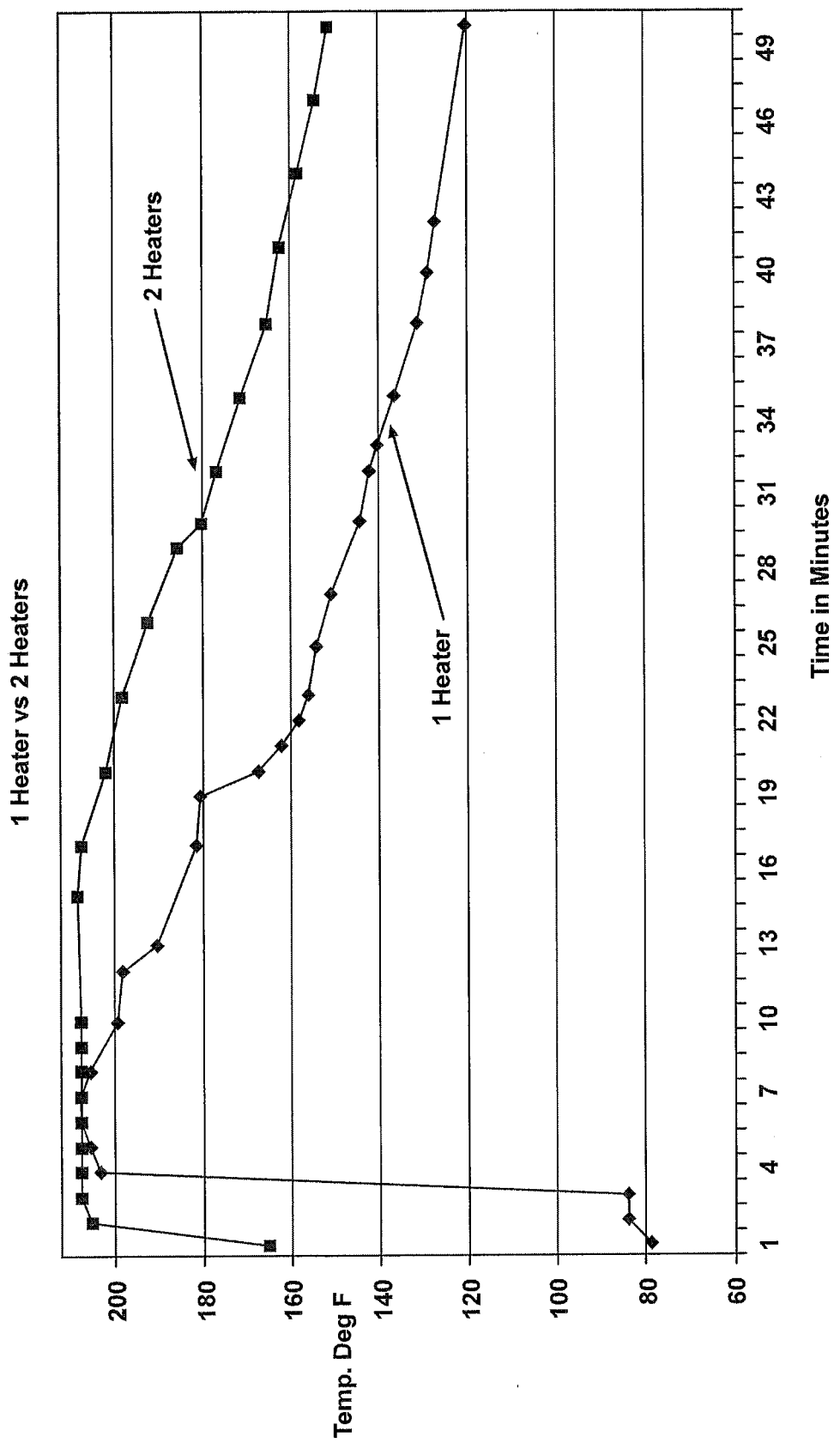
FIG. 33 is a graph depicting the temperature response of the reactor of FIGS. 1-30 as a function of time when heated by a single heater and by double heaters.

Referring to FIG. 33, in another experiment, the drop off over the subject time period is more pronounced in the last half of the time. Meanwhile, the reactor temperature is maintained close to two hundred degrees Fahrenheit for at least about 20 minutes, when two heaters are used.

Figure 34:
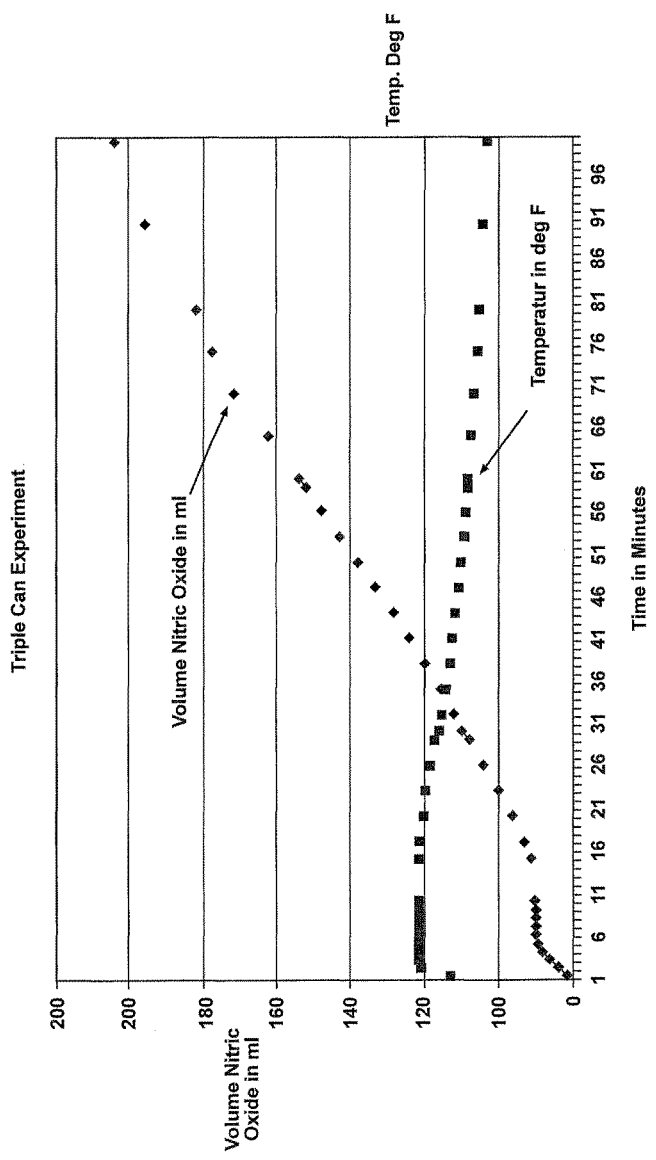
FIG. 34 is a chart depicting the released volume of nitric oxide from the reactor of FIGS. 1-30 superimposed over the temperature response thereof as a function of time.

Referring to FIG. 34, the volume of nitric oxide produced, cumulatively, over the operation of an apparatus 10 in accordance with the invention provided the illustrated results. In the chart, temperature was maintained for an extremely long period, considering that a therapy session may typically only require about 30 minutes of nitric oxide generation. The chart illustrates that the volumetric rate of nitric oxide generated was substantially constant, giving rise to a substantially straight slope or line in the time period from about 16 minutes to about 100 minutes. Meanwhile, although the measured temperature dropped during that time period from about two hundred degrees Fahrenheit to just over one hundred degrees Fahrenheit, nitric oxide production did not drop off substantially throughout. Nevertheless, the graph illustrates an apparent decline eventually.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. A method of generating nitric oxide, the method comprising:
    providing a mixture of granulated reactants comprising a nitrate compound and a nitrite compound in a reactor;
    providing a heating system comprising water in a sealed, breachable container and water-activated chemicals positioned below the mixture of reactants to heat the mixture of reactants;
    breaching the container in a manner that activates the water-activated chemicals and produces heat;
    heating the mixture of reactants to initiate a reaction within the mixture of reactants, thereby generating nitric oxide gas;
    evacuating the nitric oxide gas away from the reactor in a closed conduit
    delivering the nitric oxide gas at substantially ambient conditions to a user.

2. The method of claim 1, further comprising sizing the granules to melt and react without vaporizing at least one of the reactants in the mixture.

3. The method of claim 1, further comprising controlling the heating system to control a rate of generation of the nitric oxide gas.

4. The method of claim 1, wherein the reactants consist essentially of:
    a non-deliquescent nitrite compound;
    a nitrate compound; and
    a metal oxide.

5. The method of claim 4, wherein the non-deliquescent nitrite compound is sodium nitrite, the nitrate compound is potassium nitrate, and the metal oxide is chromic oxide.

6. The method of claim 1, wherein the water in the breachable container is salt water.

7. A method of providing nitric oxide comprising:
    selecting a generator comprising a reactor system, self-contained and containing first reactants and second reactants;
    generating heat by activating the second reactants;
    generating nitric oxide by activating the first reactants in response to the generating heat; and introducing the nitric oxide into a breathing air of a subject.

8. The method of claim 7, wherein the nitric oxide is at a concentration of from about a hundred parts per million to about five thousand parts per million in the breathing air.

9. The method of claim 7, wherein the breathing air is delivered to the subject through nasal inhalation to provide approximately five thousand parts per million of nitric oxide to the subject.

10. The method of claim 7, further comprising combining a constituent of the first reactants in a dry granular state with the other first reactants before activating the first reactants.

11. The method of claim 7, wherein selecting the generator further comprises:
    providing a first container to contain a liquid and insulate space interior to the first container;
    positioning a first chemical reactor in the first container to contain a first reaction; and
    positioning a second chemical reactor in the first container and below the first reactor to contain a second reaction heating the first reactor.

12. A method of providing nitric oxide, the method comprising:
    providing first reactants in a dry mixture, wherein the first reactants are selected to react in response to heating thereof and to generate nitric oxide gas upon heating;
    providing a first container containing the first reactants, wherein the first container further comprises providing a conduit extending from the first container to conduct the nitric oxide gas from the first container;
    providing a second container thermally insulated and substantially surrounding the first container and allowing the conduit to pass outside the second container;
    providing a third container, sealed, breachable, and containing salt water, the third container being located outside the first container and inside the second container;
    providing second reactants, dry and located inside the second container, the second reactants being selected to react in the presence of water and be exothermic upon reaction in the presence of water, thereby generating energy and heat to initiate reaction of the first reactants in the first container;
    providing a breaching assembly positioned to breach the third container upon actuation of the breaching assembly and allow the salt water to pour onto the second reactants, initiating mutual reaction of the second reactants; and
    producing nitric oxide gas.

13. The method of claim 12, further comprising:
    mixing the nitric oxide with a diluent gas to form a mixture breathable by a subject; and
    delivering, by the conduit, the breathable mixture, regulated to substantially ambient temperature and pressure.

14. The method of claim 13, wherein the first reactants consist essentially of potassium nitrate, sodium nitrite, and a metal oxide.

15. The method of claim 14, wherein the metal oxide is chromic oxide, calcined to remove substantially all water bonded thereto.

16. The method of claim 13, wherein the breathable mixture is delivered to the subject through nasal inhalation to provide approximately five thousand parts per million of nitric oxide to the subject.

\* \* \* \* \*